(12) United States Patent
Re

(10) Patent No.: US 8,282,647 B2
(45) Date of Patent: Oct. 9, 2012

(54) FEMORAL GUIDE FOR ACL REPAIR HAVING ADJUSTABLE OFFSET

(75) Inventor: Paul Re, Boston, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 461 days.

(21) Appl. No.: 12/548,760

(22) Filed: Aug. 27, 2009

(65) Prior Publication Data

US 2010/0049200 A1   Feb. 25, 2010

Related U.S. Application Data

(63) Continuation-in-part of application No. 12/366,967, filed on Feb. 6, 2009.

(60) Provisional application No. 61/066,575, filed on Feb. 21, 2008, provisional application No. 61/066,572, filed on Feb. 21, 2008.

(51) Int. Cl.
*A61B 17/58* (2006.01)
*A61B 17/60* (2006.01)
*A61F 2/30* (2006.01)

(52) U.S. Cl. .................. 606/89; 606/83; 606/99

(58) Field of Classification Search .............. 606/83, 606/88, 96, 99
See application file for complete search history.

(56) References Cited

U.S. PATENT DOCUMENTS

| | | |
|---|---|---|
| 4,911,153 A | 3/1990 | Border |
| 5,152,764 A | 10/1992 | Goble |
| 5,250,055 A | 10/1993 | Moore et al. |
| 5,314,429 A | 5/1994 | Goble |
| 5,320,115 A | 6/1994 | Kenna |
| 5,320,626 A | 6/1994 | Schmieding |
| 5,385,567 A | 1/1995 | Goble |
| 5,445,642 A | 8/1995 | McNulty |
| 5,514,144 A | 5/1996 | Bolton |
| 5,520,693 A | 5/1996 | McGuire et al. |
| 5,562,664 A | 10/1996 | Durlacher et al. |
| 5,562,669 A | 10/1996 | McGuire |
| 5,570,706 A | 11/1996 | Howell |
| 5,613,971 A | 3/1997 | Lower et al. |
| 5,891,150 A | 4/1999 | Chan |
| 5,968,050 A | 10/1999 | Torrie |
| 6,022,356 A | 2/2000 | Noyes et al. |
| 6,254,606 B1 | 7/2001 | Carney et al. |
| 6,309,396 B1 | 10/2001 | Ritland |

(Continued)

FOREIGN PATENT DOCUMENTS

CA   2654486   8/2009

(Continued)

OTHER PUBLICATIONS

PCT International Search Reports dated Oct. 19, 2010 for the corresponding application PCT/US2010/046764, Oct. 25, 2010 for the corresponding application PCT/US2010/046774, Oct. 26, 2010 for the corresponding application PCT/US2010/046769, and Oct. 27, 2010 for the corresponding application PCT/US2010/046804.

*Primary Examiner* — Andrew Yang

(57) ABSTRACT

A guide for positioning a femoral tunnel during an ACL repair. The device may include a shaft having a lumen, the lumen defining a longitudinal axis, and a distal offset projection, at least a portion of the distal offset projection extending distally from the elongated shaft, wherein the distal offset projection and the shaft are moveable relative to each other.

3 Claims, 10 Drawing Sheets

U.S. PATENT DOCUMENTS

| | | |
|---|---|---|
| 6,352,538 B2 | 3/2002 | McGuire et al. |
| 6,878,150 B1 | 4/2005 | McGuire et al. |
| 7,025,770 B2 | 4/2006 | McGuire et al. |
| 7,032,599 B2 | 4/2006 | May et al. |
| 7,458,975 B2 | 12/2008 | May et al. |
| 7,491,206 B2 | 2/2009 | Whittaker et al. |
| 7,815,646 B2 * | 10/2010 | Hart ................................ 606/96 |
| 2002/0151903 A1 | 10/2002 | Takei et al. |
| 2003/0009173 A1 | 1/2003 | McGuire et al. |
| 2004/0199170 A1 * | 10/2004 | Shluzas et al. ................ 606/105 |
| 2004/0267273 A1 | 12/2004 | Whittaker et al. |
| 2005/0203523 A1 | 9/2005 | Wenstrom et al. |
| 2005/0228399 A1 | 10/2005 | Kubo et al. |
| 2006/0074434 A1 | 4/2006 | Wenstrom, Jr. et al. |
| 2006/0149283 A1 | 7/2006 | May et al. |
| 2006/0293689 A1 | 12/2006 | Miller et al. |
| 2007/0123902 A1 | 5/2007 | Berberich et al. |
| 2007/0191853 A1 | 8/2007 | Stone |
| 2007/0233128 A1 | 10/2007 | Schmieding et al. |
| 2007/0233151 A1 | 10/2007 | Chudik |
| 2008/0103506 A1 | 5/2008 | Volpi et al. |
| 2008/0234819 A1 | 9/2008 | Schmieding et al. |
| 2009/0018654 A1 | 1/2009 | Schmieding et al. |
| 2009/0030417 A1 | 1/2009 | Takahashi |
| 2009/0157081 A1 * | 6/2009 | Homan et al. .................. 606/80 |
| 2009/0187244 A1 | 7/2009 | Dross |
| 2009/0265003 A1 | 10/2009 | Re et al. |

FOREIGN PATENT DOCUMENTS

FR 2744621 8/1997

* cited by examiner

FEMORAL GUIDE FOR ACL REPAIR HAVING ADJUSTABLE OFFSET

CROSS REFERENCE TO RELATED APPLICATIONS

This application is a continuation-in part of, and claims the benefit of priority to, U.S. patent application Ser. No. 12/366,967, filed Feb. 6, 2009, entitled "Guide for Creating a Femoral Tunnel During an ACL Reconstruction," and U.S. Provisional Patent Application Ser. No. 61/066,575, filed Feb. 21, 2008, entitled "Guide for Creating a Femoral Tunnel During an ACL Reconstruction," the disclosures of each being incorporated herein by reference in their entirety. In addition, this application is related to U.S. Provisional Patent Application Ser. No. 61/066,572, filed Feb. 21, 2008, entitled "Device for Orienting the Tibial Tunnel Position During an ACL Reconstruction" and U.S. patent application Ser. No. 12/367,007, filed Feb. 6, 2009, entitled "Device for Orienting the Tibial Tunnel Position During an ACL Reconstruction," the disclosures of each also being incorporated herein by reference in their entirety.

BACKGROUND

1. Technical Field

This invention relates to surgical apparatus and procedures in general, and more particularly to surgical apparatus and procedures for reconstructing a ligament.

2. Background of Related Art

A ligament is a piece of fibrous tissue which connects one bone to another. Ligaments are frequently damaged (e.g., detached or torn or ruptured, etc.) as the result of injury and/or accident. A damaged ligament can cause instability, impede proper motion of a joint and cause pain. Various procedures have been developed to repair or replace a damaged ligament. The specific procedure used depends on the particular ligament which is to be restored and on the extent of the damage.

One ligament which is frequently damaged as the result of injury and/or accident is the anterior cruciate ligament (i.e., the ACL). Looking first at FIGS. 1 and 2, it will be seen that the ACL 5 extends between the top of the tibia 10 and the bottom of the femur 15. A damaged ACL can cause instability of the knee joint and cause substantial pain and arthritis. For this reason, ACL reconstruction is a common procedure with more than 100,000 cases being performed in the United States annually.

Various procedures have been developed to restore and/or reconstruct a damaged ACL through a graft ligament replacement. Traditionally, this procedure is performed utilizing a trans-tibial approach. In this approach, a tibial tunnel or bone tunnel 20 is created in tibia 20 by drilling up through tibia 10. Bone tunnel 20 is then used to access an inner surface of femur 15 to drill a bone tunnel 25 up into femur 15. More particularly, once tibial tunnel 20 is created, a conventional femoral guide, often referred to as an "over-the-top" guide (FIG. 4), is used to accurately locate the femoral tunnel 25. More specifically, the "over-the-top" guide is placed through the tibial tunnel, across the joint, through the femoral notch, and then into position so that the distal finger of the guide is positioned against the backside of the femur. (FIG. 5). Proper placement of the femoral tunnel is imperative in order for the ACL graft to be properly positioned on the femur. However, as a result of using the aforementioned trans-tibial technique and the aforementioned conventional "over-the-top" femoral guide, the position of the femoral tunnel is effectively dictated by the position of the first-drilled tibial tunnel. This often results in a femoral tunnel position, and thus, an ACL reconstruction (i.e., graft orientation, etc.) that is less than optimal.

In an attempt to better position the femoral tunnel, surgeons have recently begun utilizing the so-called "medial portal technique" to drill and create the femoral tunnel. By drilling the femoral tunnel through the medial portal or an accessory portal, the femoral and tibial tunnels may be drilled independently of one another and, therefore, in a more appropriate anatomical position.

As shown in FIG. 6, when drilling the femoral tunnel through the medial portal, surgeons typically still use the same "over-the-top" femoral guide used during the aforementioned trans-tibial approach. However, because the "over-the-top" femoral guide is designed for use in a trans-tibial approach, the "over-the-top" femoral guide is not ideal for use in a medial portal approach. These "over-the-top" femoral guides generally have narrow-shaped distal tip geometries to aid in their ability to pass through the tibial tunnel. In addition, such femoral guides have an offset spatula design to hook the posterior femoral notch, thereby aiding in positioning of the guide. Aside from this spatula design, these femoral guides have no other specific referencing geometries for properly positioning the femoral tunnel.

Traditionally, surgeons utilize what is known as a "clock face" orientation in order to decide where to place the femoral tunnel within the notch of knee. This clock face orientation technique designates positions along the notch from 9 o'clock to 3 o'clock, depending on which knee is being reconstructed. This technique, while seemingly simplistic, is limited by a number of factors, one being that the positioning of the imaginary clock face along the notch is completely subjective and hence widely affected by the specific implementation of the surgeon. Therefore, it would be beneficial to have a femoral guide for use in medial approach ACL reconstruction surgery that is configured for more accurate femoral tunnel positioning. In addition, it would be beneficial if the femoral guide is designed in such a way that it might also be utilized during a trans-tibial approach.

SUMMARY

A guide for positioning a guide wire on a femur to allow a tunnel to be formed in the femur along the guide wire is provided. The guide includes an elongated shaft having proximal and distal ends, and a distal tip formed on the distal end of the elongated shaft, the distal tip having a diameter substantially similar in size to the diameter of the desired resultant femoral tunnel, wherein the elongated shaft and the distal tip are cannulated to receive the guide wire.

The distal tip further may further include at least one of opposed fingers and a distal projection. The opposed fingers or distal projection may be configured to reference a leading edge of the posterior cruciate ligament. The opposed fingers or distal projections may further be configured to reference a posterior femoral cortex. The elongated shaft may be configured to extend across a knee joint, the length of a tibial tunnel, or out of a medial port. The distal end may include a substantially circular cross-section, a substantial semi-spherical cross-section, or an unroofed cross-section.

Additionally, there is provided a method of positioning a femoral tunnel during an ACL reconstruction. The method includes the steps of providing a femoral guide including an elongated shaft having a distal end, the distal end including a diameter substantially similar in size to the diameter of the desired resultant femoral tunnel, wherein the elongated shaft and the distal end are cannulated to receive a guide wire therethrough, inserting the femoral guide into a knee joint, positioning the distal end of the guide against the femur, and inserting the guide wire through the femoral guide and into the femur.

The femoral guide may include one of opposed fingers and a distal projection configured for referencing a posterior cruciate ligament. The method may further include the step of referencing a leading edge of a posterior cruciate ligament and/or the posterior femoral cortex. The method may also include the step of flexing the knee to 120 degrees. The femoral guide may be inserted into the knee joint using a medial portal approach or a trans-tibial approach.

In accordance with various embodiments, the present invention may provide a device for positioning a femoral tunnel during ACL reconstruction, the device comprising: a shaft having a lumen, the lumen defining a longitudinal axis; and a distal offset projection, at least a portion of the distal offset projection extending distally from the elongated shaft, wherein the distal offset projection and the shaft are moveable relative to each other. The distal offset projection and the shaft may be pivotable relative to each other such that an angle between the shaft and the distal offset projection is adjustable. Additionally or alternatively, the distal offset projection and the shaft may be slideable relative to each other. The distal offset projection and the shaft may be moveable relative to each other between a first position, in which the longitudinal axis of the lumen of the shaft and the distal offset projection are disposed at a distance $d_1$ relative to each other, and a second position, in which the distance between the longitudinal axis of the lumen of the shaft and the distal offset projection is increased to a distance $d_2$ that is greater than $d_1$. In the second position, the increase in the distance between the distal offset projection and the longitudinal axis of the lumen of the shaft may be between 0 and 4 mm. At least one of the distal offset projection and the shaft may include a physical stop for preventing the distal offset projection from being moved beyond a desired distance relative to the shaft. At least one of the distal offset projection and the shaft may include one of a groove, a knurl, a protrusion and a detent for providing a tactile indication to a user that the distal offset projection and the shaft are in a particular orientation relative to each other. At least one of the distal offset projection and the shaft may include indicia for providing a visual indication to a user that the distal offset projection and the shaft are in a particular orientation relative to each other. The device may also include an actuating member for moving the shaft and the distal offset projection relative to each other. The lumen may be configured to receive a guide wire therethrough. The shaft may define, at its distal end, an unroofed portion of cross-section.

In accordance with various embodiments, the present invention may also provide a method of positioning a femoral tunnel during an ACL reconstruction, the method comprising the steps of: providing a femoral tunnel positioning guide including a shaft having a lumen, the lumen defining a longitudinal axis, and a distal offset projection, at least a portion of the distal offset projection extending distally from the elongated shaft; inserting the femoral guide into a knee joint; moving the distal offset projection and the shaft relative to each other; positioning the distal end of the guide against the femur; and inserting the guide wire through the femoral guide and into the femur. The femoral guide may be inserted into the knee joint using a medial portal technique or a trans-tibial technique.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 10 D is an end view of the femoral guide of FIGS. 10A-10C;

FIG. 10 E is top view of the distal end of the femoral guide of FIGS. 10A-10D;

DETAILED DESCRIPTION OF THE EMBODIMENTS

Figure 1:
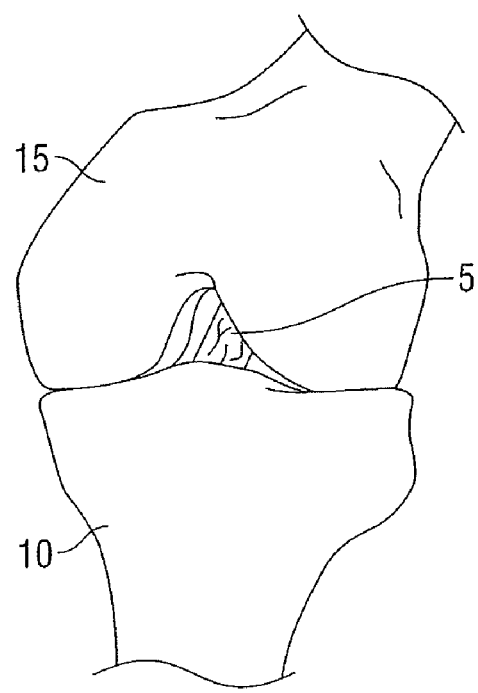
FIG. 1 is a perspective view of a knee joint showing an ACL.
Figure 2:
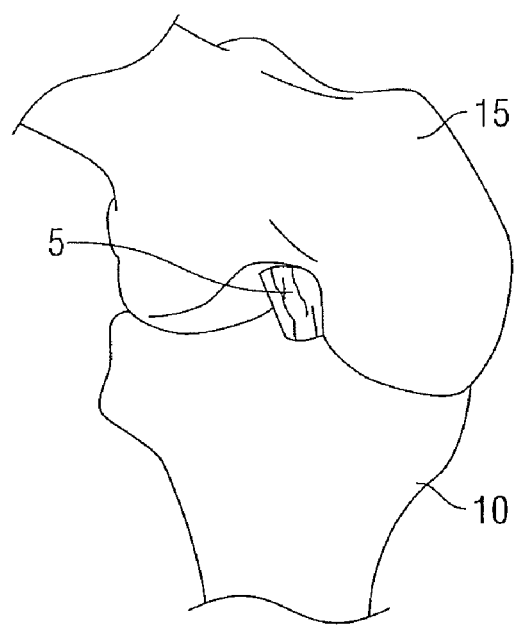
FIG. 2 is an alternate perspective view of the knee joint of FIG. 1.
Figure 3:
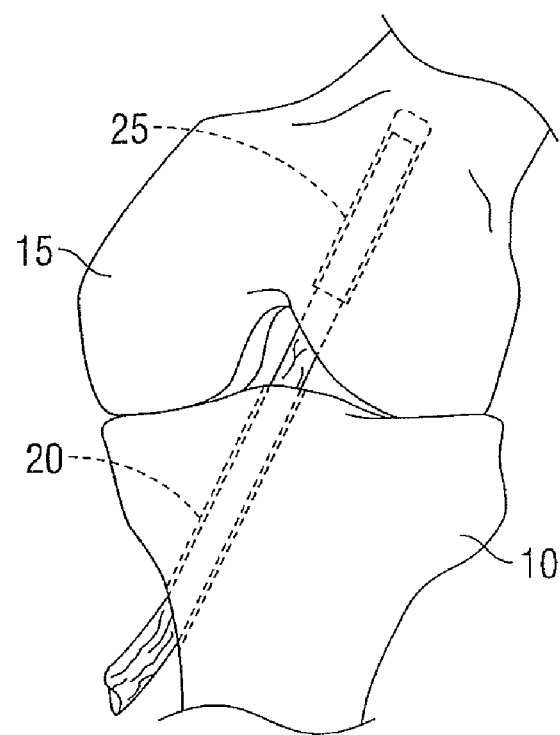
FIG. 3 is a perspective view of a knee joint including tibial and femoral tunnels (shown in phantom) and a ligament graft.
Figure 4:
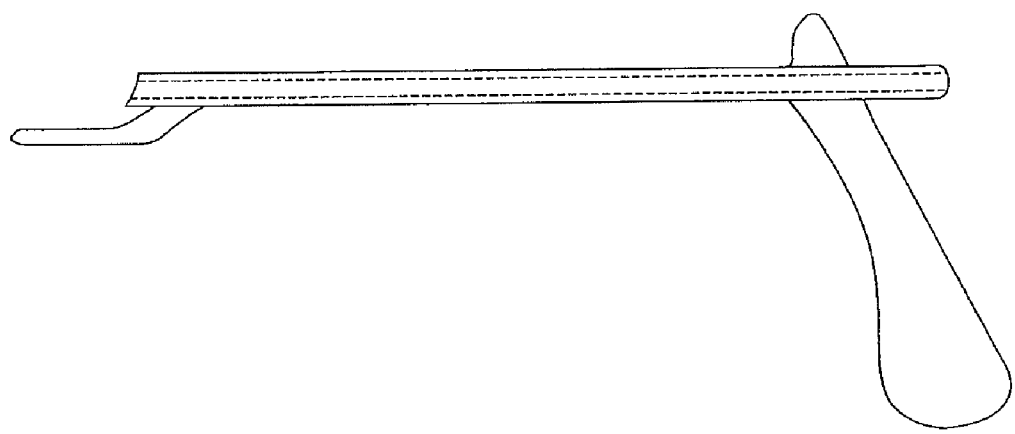
FIG. 4 is a side view of a conventional "over-the-top" femoral guide.
Figure 5:
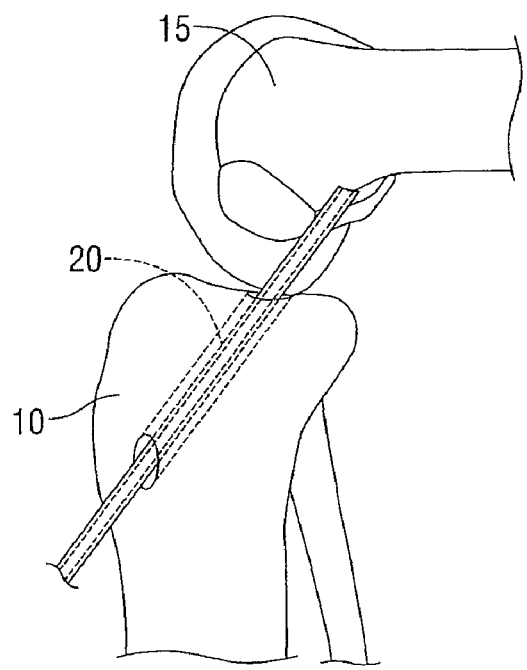
FIG. 5 is side view of a knee joint including the "over-the-top" femoral guide of FIG. 4 accessing the femur using the trans-tibial approach.
Figure 6:
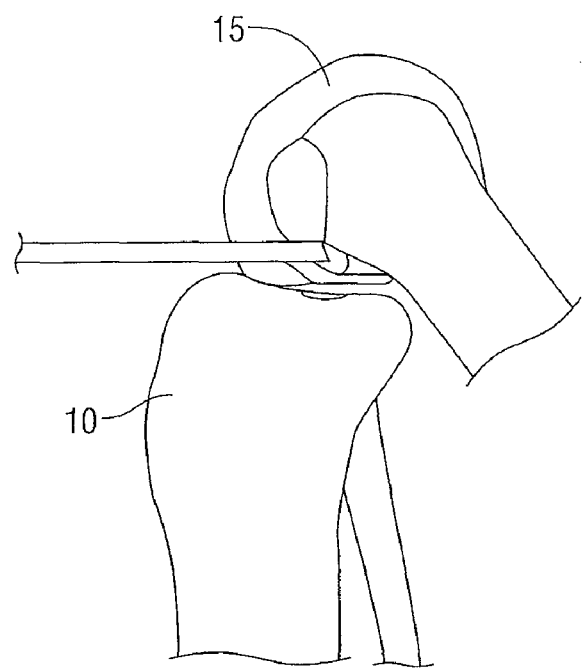
FIG. 6 is a side view of a knee joint including the "over-the-top" femoral guide of FIG. 4 access the femur using the medial portal approach.
Figure 7A:
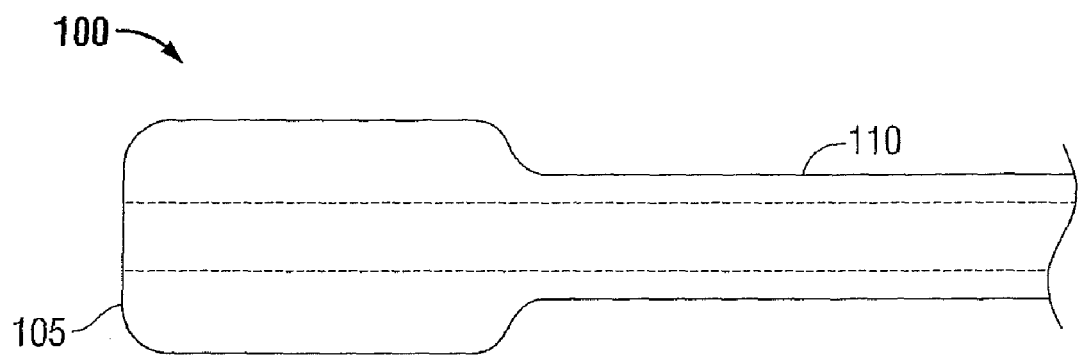
FIGS. 7A-7C are side views of the distal end of various embodiments of a femoral guide according to the present disclosure.
Figure 7B:
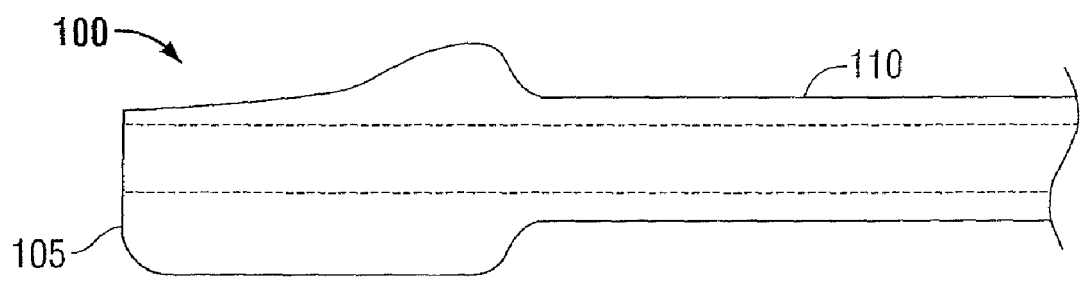
Figure 7C:
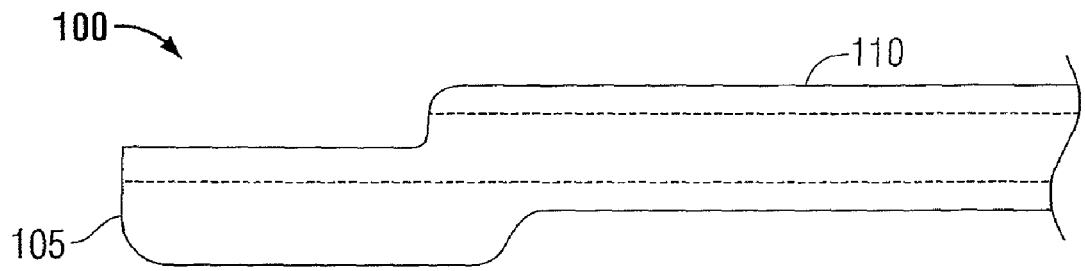
Figure 8A:
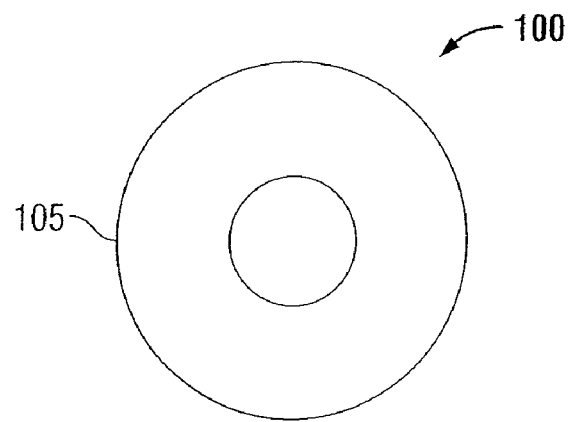
FIGS. 8A-8C are end views of the distal end of the embodiments of FIGS. 7A-7C, respectively.
Figure 8B:
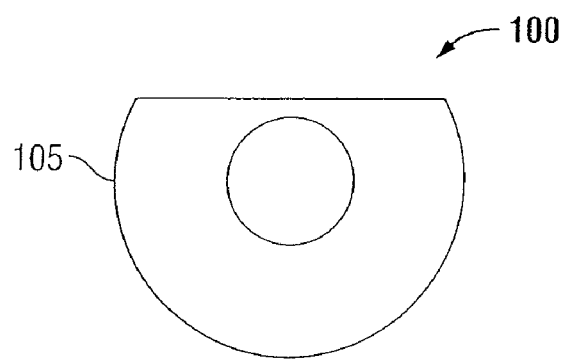
Figure 8C:
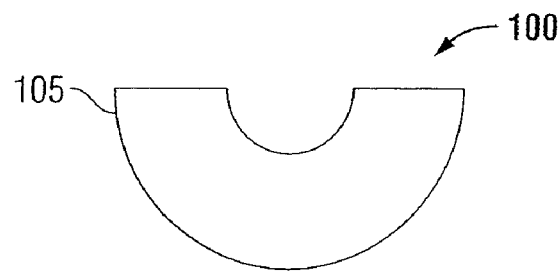
Figure 9A:
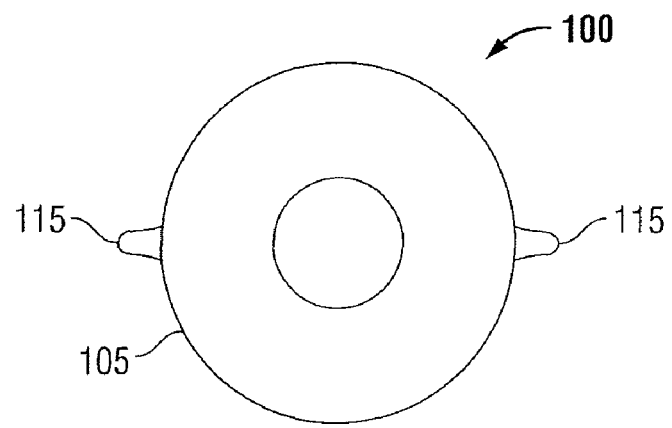
FIGS. 9A-9C are end views of the distal end of alternative embodiments of a femoral guide according to the present disclosure.
Figure 9B:
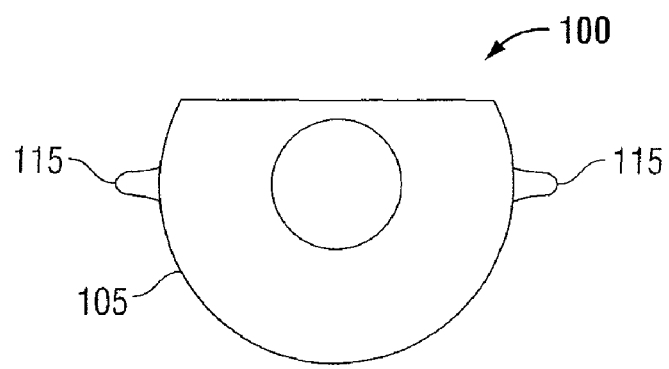
Figure 9C:
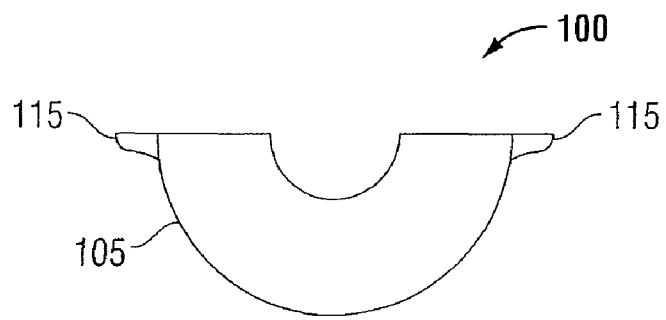
Figure 10A:
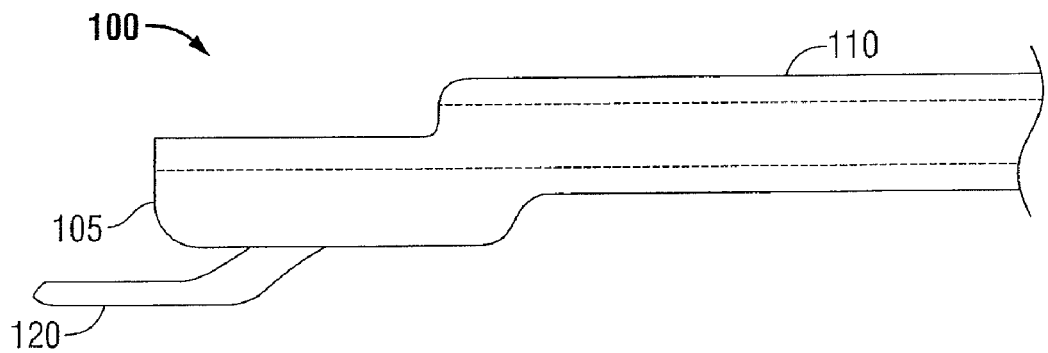
FIG. 10A is a side view of a distal end of a femoral guide according to another embodiment of the present disclosure.
Figure 10B:
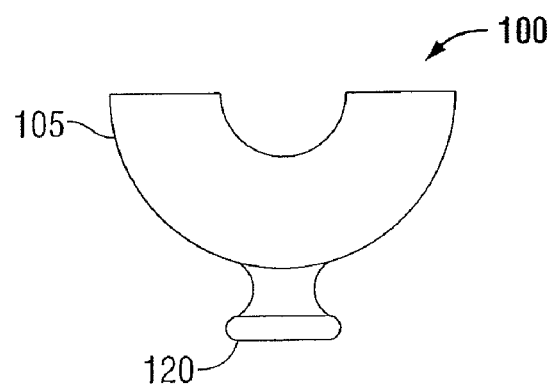
FIG. 10B is an end view of the distal end of the femoral guide of FIG. 10A.
Figure 10C:
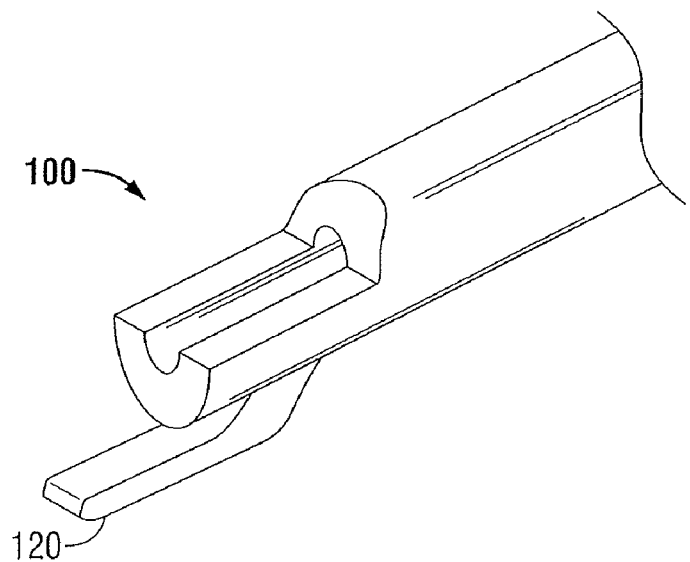
FIG. 10 C is a side view of the femoral guide of FIGS. 10A and 10B.
Figure 10D:
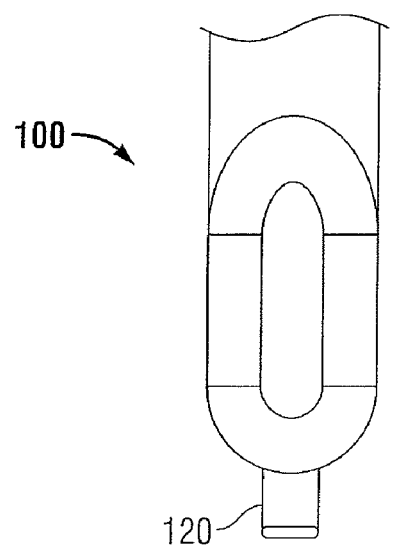
Figure 10E:
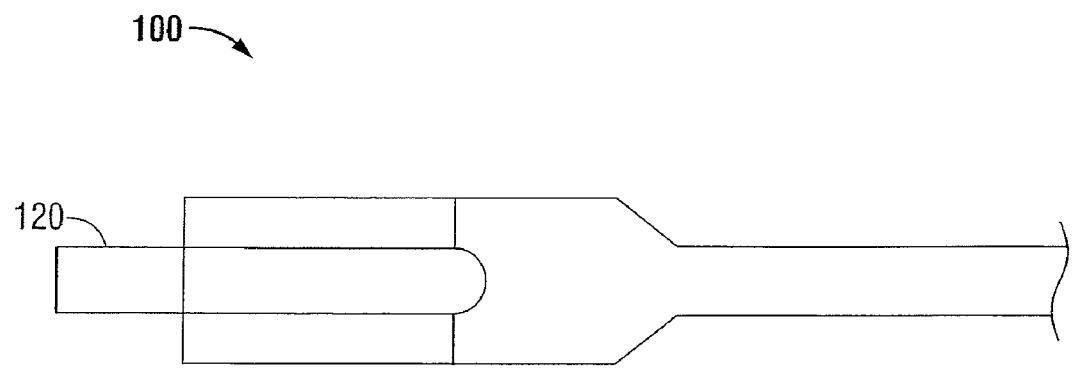

The femoral guide of the present disclosure is designed to be used in determining the position of a femoral tunnel guide wire which facilitates the positioning of a femoral tunnel during an ACL reconstruction. As with conventional femoral guides, the femoral guide of the present disclosure may reference an "over-the-top" position with an offset spatula; however, it can also be designed and utilized without such an offset spatula. This includes having no spatula, or instead having one or multiple spike projections or other similar projections to hold the spatula in position on the bone.

FIGS. 7A-10E show various embodiments of a femoral guide 100 formed in accordance with the present disclosure. Femoral guide 100 generally includes a distal tip 105 and a shaft 110 extending proximally therefrom. Distal tip 105 of femoral guide 100 may be dimensioned and configured to have the same geometry and circumference as the desired resulting femoral tunnel. In this manner, distal tip 105 acts as a visual aid to assist the surgeon in determining proper tunnel placement by providing a direct visual confirmation of where the resulting femoral tunnel will be located. Alternatively, distal tip 105 may be formed with a semi-hemispherical cross-section (FIGS. 7B, 8B and 9B), or with an "unroofed" cross-section (FIGS. 7C, 8C, 9C and 10A-E) to aid in visualization.

Shaft 110 of femoral guide 100 is configured to be of such a length so as to at least extend (i) across the knee joint, (ii) across the length of the tibial tunnel and/or (iii) out of the medial portal. Shaft 110 and distal tip 105 are cannulated so as to accept (and thereby aim) a guidewire of an appropriate circumference, length and width.

In addition, the geometry of distal end 105 of femoral guide 100 may include (i) diametrically-opposed fingers 115 (FIGS. 9A-9C), and/or (ii) a distal projection 120 (FIGS. 10A-10E). Fingers 115 and/or projection 120 serve to reference the leading edge of the posterior cruciate ligament (PCL) and the posterior femoral cortex. Using the PCL as an anatomical reference enables a surgeon to set the femoral guide wire, and therefore the resulting femoral tunnel, in a position that better avoids any impingement of the PCL after the graft ligament has been placed in position. Such ACL/PCL impingement occurs when the femoral tunnel has been improperly positioned. In this manner, femoral guide 100 is configured to avoid any such ACL/PCL impingement, by using the PCL as an anatomical reference during formation of the femoral tunnel.

Figure 11:
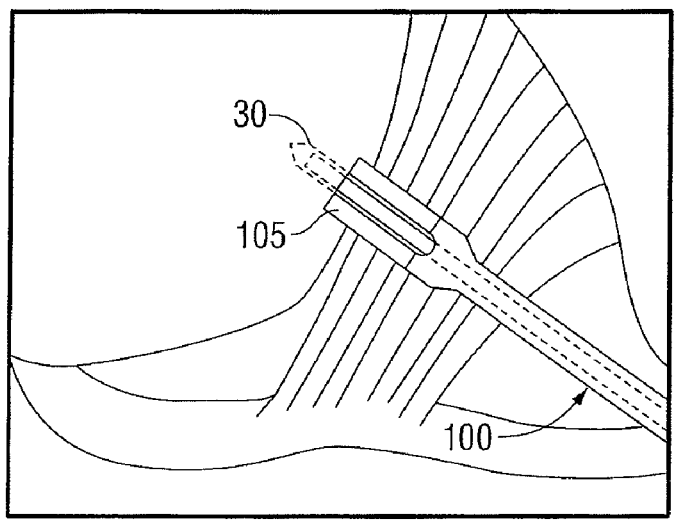
FIG. 11 is a partial cut-away view of a femoral guide according to an embodiment of the present disclosure being used in a medial portal approach.
Figure 12:
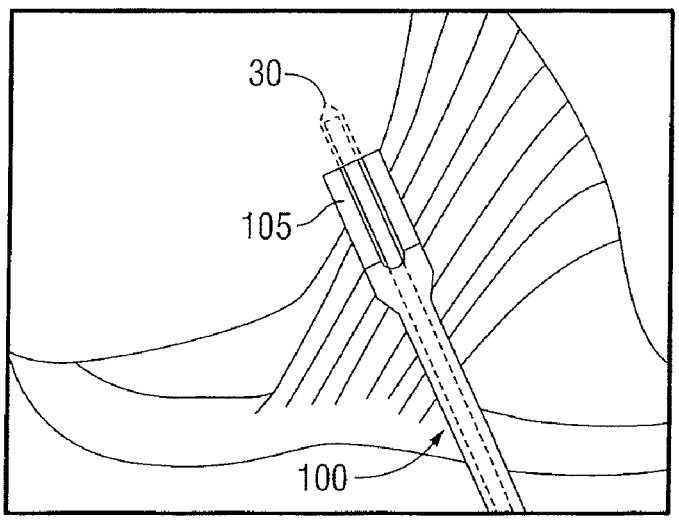
FIG. 12 is a partial cut-away view of a femoral guide according to an embodiment of the present disclosure being used in a trans-tibial approach.

As shown in FIG. 11, femoral guide 100 may be used in a medial portal approach with the knee in hyper-flexion, at approximately 120 degrees. However, it should be appreciated that femoral guide 100 may also be used with any ACL reconstruction approach, and with any angle of knee flexion. See, for example, FIG. 12, where femoral guide 100 is used during a traditional trans-tibial approach. Because of the size and/or configuration of distal end 105 of femoral guide 100, for use in the trans-tibial approach, femoral guide 100 may be halved, with one half for use with the right knee and the other half for use with the left knee.

Once the location of femoral tunnel 25 is identified by the surgeon with distal end 105 of femoral guide 100, guide wire 30 (FIG. 11) is extended through the cannulated shaft of elongated shaft 110 and into femur 15. Once guide wires 30 has been inserted into femur 15 to a desired depth, femoral guide 100 is then removed from about guide wire 30 and from the medial portal into the knee. A cannulated drill bit (not shown) is then received about guide wire 30 and through the medial portal to drill femoral tunnel 25.

Figure 13:
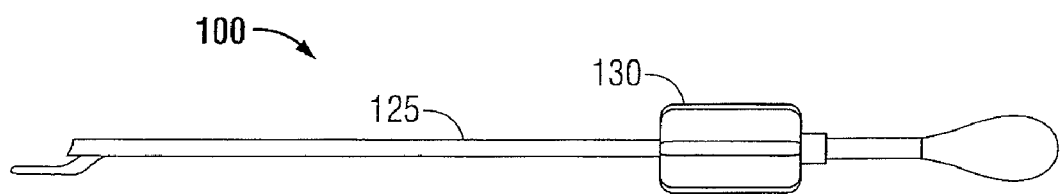
FIG. 13 is a side view of the proximal end of a femoral guide according to an embodiment of the present disclosure.

Looking next at FIG. 13, the proximal (or "butt") end 125 of femoral guide 100 is preferably provided with a docking port 130 to mate with a handle 135 to aid the surgeon in aiming the guide more easily and accurately. Handle 135 may be configured in any desired geometry so as to be ergonomically comfortable and/or to facilitate in the placement or holding of distal tip 105 in a particular position.

Femoral guide 100 provides surgeons with several significant improvements over prior art femoral guides. First, the distal portion of femoral guide 100 is configured (both in shape and diameter), to mirror that of the resulting tunnel and, therefore, the resulting graft. This gives the surgeon a visual "preview" or reference of the femoral tunnel prior to actually drilling the femoral tunnel. In addition, the distal shape of the femoral guide references the leading edge of the PCL's insertion onto the femur (i.e., the location where the PCL attaches to the femur) and places the resulting femoral tunnel in a position which avoids graft ACL/PCL impingement.

Figure 14:
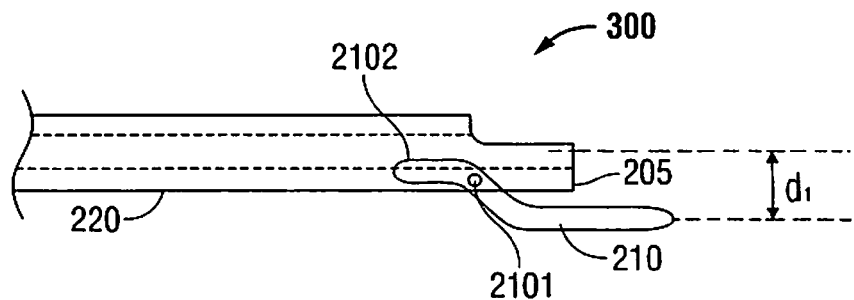
FIG. 14 is a side view of a femoral tunnel positioning guide in a first position, according to an example embodiment of the present invention.
Figure 15:
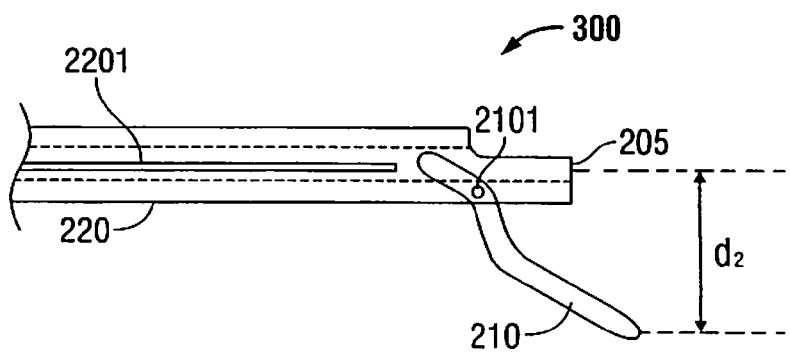
FIG. 15 is a side view of the femoral tunnel positioning guide shown in FIG. 14 in a second position.

While some of the particular embodiments shown hereinabove have the cannulated shaft 220 and the distal offset projection 210 being integrally formed and/or rigidly connected to each other, it should be recognized that the present invention may also include other embodiments in which the cannulated shaft 220 and the distal offset projection 210 are not integrally formed or not rigidly connected to each other. For example, various embodiments of the present invention may include an arrangement in which the cannulated shaft 220 and the distal offset projection 210 are separate components that are moveable relative to each other. FIGS. 14 and 15 illustrate an example embodiment of a femoral tunnel positioning device 300 having an arrangement in which the cannulated shaft 220 and the distal offset projection 210 are separate components that are moveable relative to each other. Specifically, FIGS. 14 and 15 illustrate an example embodiment of the present invention having an arrangement in which the cannulated shaft 220 is pivotably connected to the distal offset projection 210 at a pivot point 2101, enabling the cannulated shaft 220 and the distal offset projection 210 to pivot relative to each other.

Providing an arrangement in which the cannulated shaft 220 and the distal offset projection 210 are separate components that are moveable relative to each other may provide additional advantages as compared to embodiments in which the cannulated shaft 220 and the distal offset projection 210 are integrally formed and/or rigidly connected to each other. For example, and as described hereinabove, in embodiments in which the cannulated shaft 220 and the distal offset projection 210 are integrally formed and/or rigidly connected to each other, the cannulated shaft 220 and the distal offset projection 210 are typically disposed at a fixed offset distance relative to each other, e.g., typically about in the range of about 3 mm to about 8 mm. As discussed hereinabove, this offset distance is reflective of the function of the distal offset projection 210 in combination with, e.g., the position of the cannulated shaft 220 relative to the medial portal. More specifically, this offset distance reflects that, when the device is in place within a patient such that the cannulated shaft 220 is disposed within the medial portal formed by the surgeon (or is disposed within the tibial tunnel in the event that the surgeon has employed the trans-tibial technique described hereinabove), the distal offset projection 210 advantageously is configured to position the longitudinal axis of the lumen of the shaft 220 into alignment with a desired location of a femoral tunnel when the distal end 205 is in contact with a first surface of the femur and when the distal offset projection 210 is in contact with a second surface of the femur. Although having the cannulated shaft 220 and the distal offset projection 210 be integrally formed and/or rigidly connected to each other may provide the advantage of insuring that a particular offset distance between the longitudinal axis of the lumen of the shaft 220 and the distal offset projection 210 is maintained once the device is already in position within the patient's knee, it may have the disadvantage of making it more difficult for the surgeon to initially insert the device into the patient's knee and to get the device into the desired position once inserted. This potential difficulty may manifest itself due to a surgeon's general desire to have a medial portal which is as small as possible (e.g., to promote faster healing and less pain), in combination with the fact that the anatomical structures of the knee joint may result in a relatively crowded internal surgical space. Given these anatomical constraints, when the cannulated shaft 220 and the distal offset projection 210 are integrally formed and/or rigidly connected to each other at a relatively large offset distance, the surgeon may have difficulty fitting the device through a medial portal, and then may have further difficulty manipulating the device once in the internal surgical space. In addition, having an arrangement in which the cannulated shaft 220 and the distal offset projection 210 are integrally formed and/or rigidly connected to each other prevents the surgeon from adjusting the offset distance to accommodate variations in different patients' anatomy, e.g., larger offset distance may be desirable for many different reasons, such as for a large patient, for a patient that has atypical PCL attachment sites, etc.

Providing an arrangement in which the cannulated shaft 220 and the distal offset projection 210 are separate components that are moveable relative to each other may overcome some of these difficulties. For example, in embodiments in which the cannulated shaft 220 and the distal offset projection 210 are separate components that are moveable relative to each other, the cannulated shaft 220 and the distal offset projection 210 may be moveable between various positions to facilitate their insertion and/or positioning during the surgical procedure. Referring to the example embodiment illustrated in FIGS. 14 and 15, there is shown an arrangement in which the insertion and/or positioning of the device during the surgical procedure may be facilitated by having the cannulated shaft 220 be pivotably connected to the distal offset projection 210 at a pivot point 2101. Referring to FIG. 14, the femoral tunnel positioning device 300 is shown in a first position, e.g., in which the cannulated shaft 220 and the distal offset projection 210 are pivoted to a first position, such that the longitudinal axis of the lumen of the cannulated shaft 220 and the distal offset projection 210 are disposed at a distance $d_1$ to each other that is relatively small. This relatively small offset distance may enable a surgeon to more easily insert the device 300 into the medial portal and to place the device into an advantageous position prior to its final positioning. Once the surgeon has inserted the device 300 through the medial portal and placed the device into a generally desired position, the surgeon may then cause the device 300 to move to a second position, such as the position illustrated in FIG. 15. As shown in FIG. 15, in the second position, the cannulated shaft 220 and the distal offset projection 210 are pivoted to an angled position relative to each other. This angled position increases the distance between the longitudinal axis of the lumen of the cannulated shaft 220 and the distal offset projection 210 to a distance $d_2$ that is greater than $d_1$. This increased distance may be, in various embodiments of the invention, between 0 and about 4 mm, although any distance may be employed. Once adjusted, the distal offset projection 210 may then be used to accomplish the above-referenced objectives, e.g., the distal offset projection 210 may be used to position the longitudinal axis of the lumen of the shaft 220 into alignment with a desired location of a femoral tunnel when the distal end 205 is in contact with a first surface of the femur and when the distal offset projection 210 is in contact with a second surface of the femur. By enabling a surgeon to increase the angle, and thus the offset distance, between the cannulated shaft 220 and the distal offset projection 210 after the device 300 is already inserted into the medial portal and after the device has already been placed into an advantageous position, the surgeon may have relatively less difficulty fitting the device through the medial portal, and then manipulating the device into a desirable position while in the integral surgical space.

In addition, having an arrangement in which the cannulated shaft 220 and the distal offset projection 210 are moveable, e.g., pivotable, relative to each other may enable a surgeon to adjust the angle, and thus the offset distance, to accommodate variations in different patients' anatomy. Also, providing such adjustability is particularly advantageous in view of recent studies that have shown that the optimal position of a femoral tunnel may be more anteriorly positioned that previously thought. Providing such adjustability is also advantageous in that it enables surgeons that perform the medial portal technique to make any desirable adjustments to the offset distance, since it has been posited that the use of the medial portal technique, and/or the hyper-flexion of the patient's knee (as is typical in some surgeon's preferred methodology) may result in a femoral tunnel position that is more posterior than would otherwise be optimal.

As set forth above, once the surgeon has inserted the device 300 through the medial portal and placed the device into a generally desired position, the surgeon may then cause the device 300 to move to a second position, such as the position illustrated in FIG. 15. There are various ways in which the surgeon may cause the device to move between the first and second positions. For example, the femoral tunnel positioning device 300 may be configured such that the surgeon may utilize the anatomical structures within the knee joint to assist in moving the device 300 between the first and second positions. In such an arrangement, the surgeon may insert the device 300 through the medial portal while the device 300 is in the first position, e.g., such that the longitudinal axis of the lumen of the cannulated shaft 220 and the distal offset projection 210 are disposed at a distance $d_1$ to each other that is relatively small. The surgeon may then, while the device 300 is still in the first position, place the distal end 205 of the distal offset projection 210 into contact with a first surface of the femur. While maintaining the distal end 205 of the distal offset projection 210 in contact with the first surface of the femur, the surgeon may then manipulate the cannulated shaft 220 so as to cause the distal offset projection 210 to pivot relative to the cannulated shaft 220, e.g., by placing an amount of pressure on the cannulated shaft 220 which is sufficient to overcome any frictional force that may exist between the distal offset projection 210 and the cannulated shaft 220. The surgeon may continue to manipulate the cannulated shaft 220, e.g., by continuing to place pressure on the cannulated shaft 220, until the device 300 is in the second position, whereby the distance between the longitudinal axis of the lumen of the cannulated shaft 220 and the distal offset projection 210 is increased to a distance $d_2$ that is greater than $d_1$.

While in the above-described example embodiment the femoral tunnel positioning device 300 is configured such that the surgeon may utilize the anatomical structures within the knee joint to assist in moving the device 300 between the first and second positions, the present invention also contemplates other ways in which the surgeon may cause the device to move between the first and second positions. For example, the femoral tunnel positioning device 300 may include structural features that enable a surgeon to move the device 300 between the first and second positions. In such an arrangement, an actuating member 2201, as shown schematically in FIG. 15, may extend along at least a portion of the cannulated shaft 220. A distal end of the actuating member 2201 may engage a portion of the distal offset projection 210. A proximal end of the actuating member 2201 may reside on a portion of the cannulated shaft 220 that is accessible to a surgeon when the device 200 is positioned within a patient's body. In this manner, when the device 300 is positioned within a patient's body, e.g., after the surgeon has caused the distal end 205 of the distal offset projection 210 to contact a first surface of the femur, the surgeon may manipulate the proximal end of the actuating member 2201, thereby causing the distal end of the actuating member 2201 to engage the distal offset projection 210 and move the distal offset projection 210 from its first position to its second position. It should be recognized that the actuating member 2201 shown in FIG. 15 is merely one of many types of actuating members 2201 that may be employed for the purpose of moving the device 300, and specifically the distal offset projection 210, between first and second positions.

While the femoral tunnel positioning device 300 may be configured so as to enable the distal offset projection 210 and the cannulated shaft 220 to freely move, e.g., freely pivot, relative to each other, it should be recognized that, in alternative embodiments, the femoral tunnel positioning device 300 may provide features that regulate, restrict or otherwise control the free movement of the distal offset projection 210 and the cannulated shaft 220 relative to each other. For example, the femoral tunnel positioning device 300 may provide features that limit the range of motion of the distal offset projection 210 and the cannulated shaft 220 relative to each other. Such a feature may include physical stops that prevent the distal offset projection 210 from being over-pivoted relative to the cannulated shaft 220. For example, the distal offset projection 210 and the cannulated shaft 220 may include one or more physical stops that contact each other when, e.g., the distal offset projection 210 and the cannulated shaft 220 are in a first position and/or when the distal offset projection 210 and the cannulated shaft 220 are pivoted to a second position and prevent the distal offset projection 210 and the cannulated shaft 220 from being pivoted beyond the desired angles relative to each other. Such physical stops may be features that extend radially from the distal offset projection 210 and/or the cannulated shaft 220, e.g., corresponding nubs or shoulders. Additionally or alternatively, such physical stops may simply be accomplished via the relative shapes of the distal offset projection 210 and/or cannulated shaft 220, e.g., the proximal end 2102 of the distal offset projection 210 fitting within a slot or bore of the cannulated shaft 220, the bore or slot having a shape that prevents over-pivoting of the distal offset projection 210 when moved.

While the femoral tunnel positioning device 300 may provide features that regulate or restrict the free movement of the distal offset projection 210 and the cannulated shaft 220 relative to each other by limiting the range of motion of the distal offset projection 210 and the cannulated shaft 220 relative to each other, it should be recognized that, additionally or alternatively, the femoral tunnel positioning device 300 may provide features that regulate or restrict the free movement of the distal offset projection 210 and the cannulated shaft 220 relative to each other by providing resistance to the movement of the distal offset projection 210 and the cannulated shaft 220 relative to each other. Such features may include grooves or knurls on one or more of the distal offset projection 210 and the cannulated shaft 220. Such features may generate increased friction between the distal offset projection 210 and the cannulated shaft 220 when moved, as compared to a relatively lower friction that would be present without such features. The friction generated by such features may be relatively low, such that there is little resistance needed to move the distal offset projection 210 and the cannulated shaft 220 relative to each other. Alternatively, such friction may be relatively high, such that, absent a force exerted by the surgeon, the distal offset projection 210 and the cannulated shaft 220 will remain in their relative positions. Such features may also include one or more of protrusions and/or detents on one or more of the distal offset projection 210 and the cannulated shaft 220. Such protrusions and/or detents may be located at specific positions of the distal offset projection 210 and/or the cannulated shaft 220. For example, in an embodiment, such protrusions and/or detents are located at specific positions of the distal offset projection 210 and/or the cannulated shaft 220 such that a surgeon will experience a tactile indication when the distal offset projection 210 and the cannulated shaft 220 are at specific positions relative to each other, e.g., when they are in a first position and/or when the distal offset projection 210 and the cannulated shaft 220 are pivoted to a second position. Of course, any number of features, e.g., protrusions and/or detents, indicating any number of relative positions of the distal offset projection 210 and the cannulated shaft 220, may be employed.

In addition, the femoral tunnel positioning device 300 may provide indicia that provide an indication to the surgeon of the position of the distal offset projection 210 and the cannulated shaft 220 relative to each other. Such indicia may be located at specific positions of the distal offset projection 210 and/or the cannulated shaft 220. For example, in an embodiment, such indicia may be located at specific positions of the distal offset projection 210 and/or the cannulated shaft 220 such that a surgeon will be able to ascertain the relative positions of the distal offset projection 210 and the cannulated shaft 220. Of course, any number of indicia, indicating any number of relative positions of the distal offset projection 210 and the cannulated shaft 220, may be employed. Furthermore, such indicia may be located at specific positions of the distal offset projection 210 and/or the cannulated shaft 220 that coincide with the specific positions of protrusions and/or detents of the distal offset projection 210 and/or the cannulated shaft 220, thus providing a surgeon with both a visual and a tactile indication when the distal offset projection 210 and the cannulated shaft 220 are at specific positions relative to each other.

Figure 16:
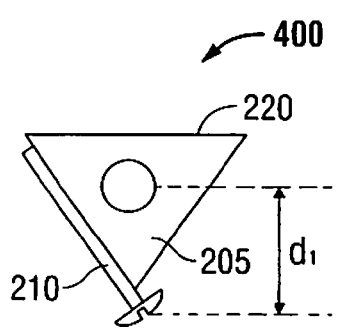
FIG. 16 is a front view of a femoral tunnel positioning guide in a first position, according to another example embodiment of the present invention.
Figure 17:
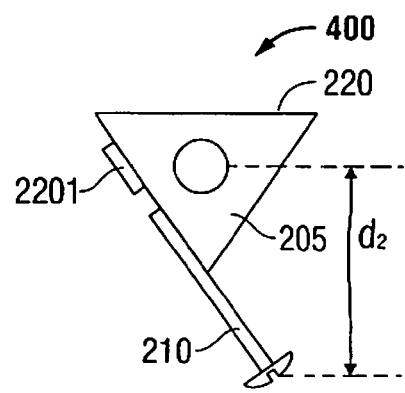
FIG. 17 is a front view of the femoral tunnel positioning guide shown in FIG. 16 in a second position.

While some of the above-described embodiments of the present invention include an arrangement in which the distal offset projection 210 is a separate component from, and is pivotably moveable relative to, the cannulated shaft 220, it should be recognized that the present invention may also include other embodiments in which the distal offset projection 210 is moveable relative to the cannulated shaft 220 in a manner other than by pivoting. For example, various embodiments of the present invention may include an arrangement in which the distal offset projection 210 is slideably moveable relative to the cannulated shaft 220. FIGS. 16 and 17 is a front view of a femoral tunnel positioning device 400, and illustrate an example embodiment of the present invention having an arrangement in which a distal offset projection 210 is a separate component that is slideably moveable relative to the cannulated shaft 220 (in this embodiment, the cannulated shaft 220 is illustrated as having a triangular cross-section—of course it should be recognized that any cross-sectional shape may be employed). Specifically, FIGS. 16 and 17 illustrate an example embodiment of the present invention having an arrangement in which a distal offset projection 210 is slideably connected to an outer surface of the cannulated shaft 220, enabling the distal offset projection 210 to slide relative to the cannulated shaft 220.

Providing an arrangement in which the distal offset projection 210 is a separate component from, and is moveable relative to, the cannulated shaft 220, may provide additional advantages as compared to embodiments in which the cannulated shaft 220 and the distal offset projection 210 are integrally formed and/or rigidly connected to each other. For example, and similar to the advantages described hereinabove in connection with the embodiments of FIGS. 14 and 15, having an arrangement in which the distal offset projection 210 is a separate component from, and is slideably moveable relative to, the cannulated shaft 220 may help a surgeon to facilitate the insertion and/or positioning of the device during the surgical procedure. Referring to the example embodiment illustrated in FIGS. 16 and 17, there is shown an arrangement in which the insertion and/or positioning of the device during the surgical procedure may be facilitated by having the distal offset projection 210 be slideably connected to the device 400 along the outer surface of the cannulated shaft 220. Referring to FIG. 16, the femoral tunnel positioning device 400 is shown in a first position, e.g., such that the longitudinal axis of the lumen of the cannulated shaft 220 and the distal offset projection 210 are disposed at a distance $d_1$ relative to each other that is relatively small. This relatively small offset distance may enable a surgeon to more easily insert the device 400 into the medial portal (or the tibial tunnel if a surgeon uses the trans-tibial technique described hereinabove) and to place the device 400 into an advantageous position prior to its final positioning. Once the surgeon has inserted the device 400 through the medial portal and placed the device into a generally desired position, the surgeon may then cause the distal offset projection 210 to move to a second position, such as the position illustrated in FIG. 17. As shown in FIG. 17, in the second position, the distance between the longitudinal axis of the lumen of the cannulated shaft 220 and the distal offset projection 210 is increased to a distance $d_2$ that is greater than $d_1$. This increase in the distance is preferably from 0 to about 4 mm, although any increase in this distance is contemplated. Once adjusted, the distal offset projection 210 may then be used to accomplish the above-referenced objectives, e.g., the distal offset projection 210 may be used to position the longitudinal axis of the lumen of the shaft 220 into alignment with a desired location of a femoral tunnel when the distal end 205 is in contact with a first surface of the femur and when the distal offset projection 210 is in contact with a second surface of the femur. By enabling a surgeon to increase the offset distance between the cannulated shaft 220 and the distal offset projection 210 after the device 300 is already inserted into the medial portal and after the device has already been placed into an advantageous position, the surgeon may have relatively less difficulty fitting the device through the medial portal, and then manipulating the device into a desirable position while in the internal surgical space. In addition, having an arrangement in which the cannulated shaft 220 and the distal offset projection 210 are moveable, e.g., slideable, relative to each other may enable a surgeon to adjust the offset distance to accommodate variations in different patients' anatomy.

Similar to some of the above-described embodiments, there are various ways in which the surgeon may cause a device, such as the device shown in FIGS. 16 and 17, to move between the first and second positions. For example, the femoral tunnel positioning device 400 of FIG. 16 may be configured such that the surgeon may utilize the anatomical structures within the knee joint to assist in moving the device 400 between the first and second positions. In such an arrangement, the surgeon may insert the device 400 through the medial portal while the device 400 is in the first position, e.g., such that the longitudinal axis of the lumen of the cannulated shaft 220 and the distal offset projection 210 are disposed at a distance $d_1$ relative to each other that is relatively small. The surgeon may then cause the distal offset projection 210 to contact an anatomical feature within the patient's knee. With the distal offset projection 210 in contact with the anatomical feature within the patient's knee, a surgeon may then place an amount of pressure on the distal offset projection 210 which is sufficient to overcome any frictional force that may exist between the distal offset projection 210 and the cannulated shaft 220 so as to cause the distal offset projection 210 to slide relative to the cannulated shaft 220. The surgeon may continue to place such pressure on the distal offset projection 210 until the device 400 is in the second position, e.g., in which the distance between the longitudinal axis of the lumen of the cannulated shaft 220 and the distal offset projection 210 is increased to a distance $d_2$ that is greater than $d_1$ as shown in FIG. 17. With the distal offset projection 210 so disposed, the surgeon may then place the distal offset projection 210 into contact with a surface of the femur to thereby align the longitudinal axis of the lumen of the cannulated shaft 220 with a desired position of the femoral tunnel to be formed.

As mentioned previously, while various above-described example embodiments include arrangements in which the femoral tunnel positioning device is configured such that the surgeon may utilize the anatomical structures within the knee joint to assist in moving the device between the first and second positions, the present invention also contemplates other ways in which the surgeon may cause the device 400 to move between the first and second positions. For example, the femoral tunnel positioning device 400 shown in FIGS. 16 and 17 may include structural features that enable a surgeon to move the device 400 between the first and second positions. In such an arrangement, an actuating member 2201, as shown schematically in FIG. 17, may extend along at least a portion of the cannulated shaft 220. A distal end of the actuating member 2201 may engage a portion of the distal offset projection 210. A proximal end of the actuating member 2201 may reside on a portion of the cannulated shaft 220 that is accessible to a surgeon when the device 400 is positioned within a patient's body. In this manner, when the device 400 is positioned within a patient's body, e.g., either before or after the surgeon has contacted the distal end 205 of the cannulated shaft 220 to a surface of the femur, the surgeon may manipulate the proximal end of the actuating member 2201, thereby causing the distal end of the actuating member 2201 to engage the distal offset projection 210 and move the distal offset projection 210 from its first position to its second position. It should be recognized that the actuating member 2201 shown in FIG. 17 is merely one of many types of actuating members 2201 that may be employed for the purpose of moving the device 400, and specifically the distal offset projection 210, between its first and second positions.

As mentioned above in connection with the embodiments described in FIGS. 14 and 15, the femoral tunnel positioning device 400 as shown in FIGS. 16 and 17 may be configured so as to enable the distal offset projection 210 to freely move, e.g., freely pivot, relative to the cannulated shaft 220, and/or the femoral tunnel positioning device 400 may provide features that regulate, restrict or otherwise control the free movement of the distal offset projection 210 relative to the cannulated shaft 220. For example, the femoral tunnel positioning device 400 may provide features that limit the range of motion of the distal offset projection 210 relative to the cannulated shaft 220, such as physical stops that prevent the distal offset projection 210 from being over-pivoted, e.g., corresponding nubs or shoulders, and/or via the relative shapes of the distal offset projection 210 and/or cannulated shaft 220 such as slots and bores. Additionally or alternatively, the femoral tunnel positioning device 400 may provide features that regulate or restrict the free movement of the distal offset projection 210 relative to the cannulated shaft 220 of the device by providing resistance therebetween, e.g., grooves, knurls, protrusions, detents, etc. that generate increased friction between the distal offset projection 210 and/or the cannulated shaft 220 when moved, as compared to a relatively lower friction that would be present without such features.

It should be understood that many additional changes in the details, materials, steps and arrangements of parts, which have been herein described and illustrated in order to explain the nature of the present disclosure, may be made by those skilled in the art while still remaining within the principles and scope of the disclosure.

What is claimed is:

1. A method of positioning a femoral tunnel during an ACL reconstruction, the method comprising the steps of:
   providing a femoral tunnel positioning guide including a shaft having a distal end and defining a lumen, the lumen defining a longitudinal axis, and a distal offset projection, at least a portion of the distal offset projection extending distally from the elongated shaft;
   inserting the femoral guide into a knee joint, wherein a distal end of the distal offset projection is spaced laterally of the distal end of the shaft a distance $d_1$;
   moving the distal offset projection and the shaft relative to each other;
   positioning the distal offset projection against a first surface of the femur and the distal end of the shaft against a second surface of the femur, wherein the distal offset projection is in a second position wherein the distal end of the distal offset projection is spaced laterally of the distal end of the shaft a distance $d_2$, wherein $d_2$ is greater than $d_1$; and
   inserting the guide wire through the femoral guide and into the femur.

2. The method of claim 1, wherein the femoral guide is inserted into the knee joint using a medial portal technique.

3. The method of claim 1, wherein the femoral guide is inserted into the knee joint using a trans-tibial technique.

* * * * *